(12) United States Patent
Liu et al.

(10) Patent No.: US 6,528,540 B2
(45) Date of Patent: *Mar. 4, 2003

(54) ESMOLOL FORMULATION

(75) Inventors: Jie Liu, Scotch Plains, NJ (US); Satish K. Pejaver, Bridgewater, NJ (US); George Owoo, North Plainfield, NJ (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/016,260

(22) Filed: Oct. 30, 2001

(65) Prior Publication Data

US 2002/0147239 A1 Oct. 10, 2002

Related U.S. Application Data

(63) Continuation-in-part of application No. 09/759,547, filed on Jan. 12, 2001, now Pat. No. 6,310,094.

(51) Int. Cl.$^7$ ................................................ A61K 31/24
(52) U.S. Cl. ....................................................... 514/538
(58) Field of Search .......................................... 514/538

(56) References Cited

U.S. PATENT DOCUMENTS 6,310,094 B1 * 10/2001 Liu et al. ..................... 514/538

* cited by examiner

*Primary Examiner*—Raymond Henley, III
(74) *Attorney, Agent, or Firm*—Kenneth E. Jaconetty

(57) ABSTRACT

An aqueous, sterile pharmaceutical composition suitable for parenteral administration for the treatment of cardiac conditions, comprising methyl-3-[4-(2-hydroxy-3-isopropylamino)propoxy]phenylpropionate hydrochloride (esmolol hydrochloride), a buffering agent and an osmotic-adjusting agent, as well as a method for its manufacture, are disclosed.

16 Claims, No Drawings

ESMOLOL FORMULATION

CROSS-REFERENCE TO RELATED PATENT APPLICATIONS

This patent application is a continuation-in-part of U.S. patent application Ser. No. 09/759,547, filed Jan. 12, 2001, issued as U.S. Pat. No. 6,310,094.

BACKGROUND OF THE INVENTION

Esmolol hydrochloride is a short-acting beta-blocker used for treatment or prophylaxis of cardiac disorders in mammals. Most of the currently available beta-blockers are stable drugs which can be administered to cardiac patients over relatively long periods of time. However, it is often desirable in the critical care setting to quickly reduce heart work or improve rhythmicity during a cardiac crisis, e.g., during or shortly after a myocardial infarction. Conventional beta-blocking agents can be employed for such treatment, but their long durations of action can cause undesirable side effects.

Esmolol hydrochloride contains an ester functional group and possesses the typical beta-adrenergic blocking activity. However, it differs from conventional beta-blocking compound in that esmolol hydrochloride has a short duration in vivo due to the presence of the ester group. Thus, esmolol hydrochloride is advantageous compared to the conventional beta-blockers because of its unique short-acting activity. However, the ester group in esmolol hydrochloride is found to be unstable in an aqueous environment because of it extreme susceptibility to hydrolytic degradation.

The stability of esmolol in water is mediated by the rate of acid/base hydrolysis of the labile aliphatic methyl ester group. In the past, the rate of degradation of esmolol hydrochloride has been reduced by the use of acetate as a buffer, maintaining the pH as close to 5.0 as possible, minimizing the concentration of esmolol in the solution, and minimizing the concentration of buffer used. Prior art formulations maintain a reasonably long shelf-life, however, they suffer from severe degradation upon autoclaving. As a result, prior art formulations are prepared aseptically. C.f. U.S. Pat. Nos. 4,857,552 and 5,107,609. U.S. Pat. No. 4,857,552 discloses a ready-to-use formulation suitable for vial packaging containing esmolol in an aqueous buffer solution. U.S. Pat. No. 5,107,609 discloses a concentrated formulation suitable for ampul packaging containing esmolol in an aqueous buffer solution, with propylene glycol and ethanol added to increase solubility of the esmolol. Prior to administration, this ampul formulation is diluted to appropriate dosage level with a compatible isotonic solution such as one containing dextrose, lactated Ringer's solution, sodium chloride or potassium chloride.

However, microbiological contamination of the product during dilution/aseptic handling is possible in both vial and ampul presentations. Therefore, terminal sterilization is typically preferred by regulatory authorities as a way of reducing microbiological burden and to ensure the safety of the finished product.

BRIEF SUMMARY OF THE INVENTION

The present invention relates to an aqueous, sterile pharmaceutical composition suitable for parenteral administration for the treatment of cardiac conditions comprising methyl-3-[4-(2-hydroxy-3-isopropylamino)propoxy]phenylpropionate hydrochloride (esmolol hydrochloride), a buffering agent and an osmotic-adjusting agent, and further relates to a method for its manufacture in a container.

DETAILED DESCRIPTION OF THE INVENTION

The present invention provides a stable, parenteral composition containing esmolol hydrochloride and a pharmaceutically acceptable buffering agent and an osmotic adjusting agent to adjust the tonicity of the solution. The composition is packaged in a sealed container and subjected to terminal sterilization via autoclaving to reduce the microbiological burden of the formulation. Esmolol hydrochloride formulations of the prior art cannot survive autoclaving. The present invention is stable against hydrolytic degradation and other adverse chemical reactions, and possesses a pharmaceutically-acceptable shelf-life.

"Stable", as used in the context of this application, means remaining in a state or condition that is suitable for administration to a patient. Formulations according to the present invention are found to be stable when maintained at room temperature for at least 12 months, and are generally stable at room temperature for 12 to 24 months.

A "sterile" composition, as used in the context of this application, means a composition that has been brought to a state of sterility and has not been subsequently exposed to microbiological contamination, i.e. the container holding the sterile composition has not been compromised. Sterile compositions are generally prepared by pharmaceutical manufacturers in accordance with current Good Manufacturing Practice ("cGMP") regulations of the U.S. Food and Drug Administration.

The product can take the form of a sterile, ready-to-use formulation for infusion. This avoids the inconvenience of diluting a concentrated esmolol small volume parenteral formulation into infusion diluents prior to infusion, as well as eliminates the risk of microbiological contamination during aseptic handling and any potential calculation or dilution error. Such formulations, not being prepared from a concentrate, will be essentially free from propylene glycol and ethanol. The product can also take the form of a concentrated formulation which must be diluted prior to administration.

The aqueous, sterile pharmaceutical composition of the present invention is suitable for parenteral administration to a patient. For example, the composition may be administered in the form of a bolus injection or intravenous infusion. Suitable routes for parenteral administration include intravenous, subcutaneous, intradermal, intramuscular, intraarticular, and intrathecal. The ready-to-use formulation of the invention is preferably administered by intravenous infusion.

Containers suitable according to the present invention are those known in the art. They include vial, syringe, bag, bottle and ampul presentations. Containers may be fabricated from glass or from polymeric materials. Ready-to-use formulations are typically packaged in vials, syringes, bags and bottles, while concentrated formulations are typically packaged in ampuls.

The pH of the composition greatly effects its stability. The pH should be between 3.5 and 6.5, preferably between 4.5 and 5.5, more preferably about 5.0. The pH can be adjusted as known in the art by addition of sodium hydroxide or hydrochloric acid.

Esmolol hydrochloride is present in the instant composition in an amount ranging from 0.1–500 mg/ml. Ready-to-use formulations may contain 0.1–100 mg/ml, preferably 1–20 mg/ml, more preferably 1–10 mg/ml. Concentrated formulations may contain 100–500 mg/ml, preferably 100–250 mg/ml.

Suitable buffering agents are known in the art, and are present in the composition in a concentration ranging from 0.01–2 M. Ready-to-use formulations typically have buffering agent concentrations of 0.01–0.5 M, preferably 0.02–0.1 M. Concentrated formulations typically have buffering agent concentrations of 0.5–2 M. Buffering agents include acetate, glutamate, citrate, tartrate, benzoate, lactate, gluconate, phosphate and glycine. The preferred buffering agent comprises a combination of sodium acetate and glacial acetic acid.

Suitable osmotic-adjusting agents are known in the art, and are present in the composition in an amount ranging from 1–500 mg/ml. Osmotic-adjusting agents include sodium chloride, dextrose, sodium bicarbonate, calcium chloride, potassium chloride, sodium lactate, Ringer's solution and lactated Ringer's solution. Preferred are sodium chloride and dextrose. Ready-to-use formulations may contain 1–100 mg/ml osmotic-adjusting agent; preferably 4–60 mg/ml sodium chloride, more preferably 4–10 mg/ml sodium chloride; or dextrose, with or without sodium chloride, in an amount ranging from 25–60 mg/ml. Dextrose is preferably present in the composition of the present invention at a level no greater than 5% (weight by weight) in combination with sodium chloride. Concentrated formulations may contain 50–500 mg/ml osmotic-adjusting agent.

Compositions according to the present invention can be prepared into small volume parenteral (SVP) and large volume parenteral (LVP) dosage forms. The dosage forms can be held in any suitable container. Suitable containers include, for example, glass or polymeric vials, ampuls, syringes or bags with sizes ranging from 1 ml to 500 ml. SVP ready-to-use solutions are typically filled into ampules and vials in 1–100 mL presentations. In addition, syringes can be used as the container for a ready-to-use SVP, which are sold as "pre-filled syringes". The LVP presentations can be contained in bags or bottles.

Polymeric containers are preferably flexible and can contain or be free of polyvinylchloride (PVC). Preferred containers are free of PVC, such as those disclosed in U.S. Pat. Nos. 5,849,843 and 5,998,019. Polymeric containers can further be provided with a moisture barrier as a secondary packaging system to prevent the loss of water during storage and to further ensure the stability of the formulation. A preferred moisture barrier is an aluminum overpouch.

Procedures for filling compositions of the present invention in containers, and their subsequent processing are known in the art. These procedures are used to produce sterile pharmaceutical drug products often required for health care. Such processing techniques preferably use a sterilization process to destroy or eliminate any microorganisms that may be present in the esmolol formulations following preparation. For example, terminal sterilization can be used to destroy all viable microorganisms within the final, sealed package containing the esmolol formulation. An autoclave is commonly used to accomplish terminal heat-sterilization of drug products in their final packaging.

Typical autoclave cycles in the pharmaceutical industry to achieve terminal sterilization of the final product are 121° C. for 15 minutes. The esmolol hydrochloride composition of the present invention can be autoclaved at a temperature ranging from 115 to 130° C. for a period of time ranging from 5 to 40 minutes with acceptable stability. Autoclaving is preferably carried out in the temperature range of 119° C. to 122° C. for a period of time ranging from 10 to 36 minutes.

Alternatively, sterile pharmaceutical compositions according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampul, bag, bottle, or syringe) are then filled under aseptic conditions.

The following examples further illustrate the invention but, of course, should not be construed as in any way limiting its scope.

EXAMPLE 1

The following describes the preparation of ready-to-use infusion bags of the present invention containing 10 mg/ml esmolol HCl solution. The concentration of each ingredient of the composition is as follows:

| Ingredient | Amount/ml Solution |
| --- | --- |
| Esmolol HCl | 11 mg/ml |
| Sodium Chloride (osmotic) | 5.9 mg/ml |
| Sodium Acetate Trihydrate (buffer) | 2.8 mg/ml (0.02M) |
| Glacial Acetic Acid (buffer) | 0.546 mg/ml (0.01M) |
| Sodium Hydroxide/Hydrochloric Acid | pH adjustment to 5.0 |
| Water for Injection, USP | qs |

The equipment and glassware for compounding, filtering, and filling are properly washed and depyrogenated. The filter assembly, filling tube assembly, and other parts and equipment are sterilized.

Eighty percent (80%) of the final volume of cool Water for Injection is collected in a calibrated compounding tank. Sodium chloride is added to the tank and the solution is stirred until sodium chloride is dissolved. Glacial acetic acid and sodium acetate are then added to the tank. The solution is further stirred until all excipients are dissolved. The tank is adjusted to 90% of final volume with Water for Injection and mixed. Approximately 2 liter of this solution (buffer solution) is removed for use in preparation of the slurry solution. Esmolol hydrochloride is weighed and added to the 2 liter of the buffer solution to form a slurry solution. This slurry is then added to the compounding tank and the solution is mixed. The solution is then adjusted to pH 5.0 with 1 N sodium hydroxide or hydrochloric acid. The solution is brought to final volume with Water for Injection and mixed.

The solution is then filled into 250 ml non-PVC flexible bags (IntraVia™ flexible plastic container (PL 2408-3 non-PVC multi-layer plastic film) with one standard PL 146® PVC membrane tube, one PL 2409-3 multi-layer plastic co-extruded administration port tube, one PL 141 PVC blue-tip closure (administration port protector), available from Baxter Healthcare Corporation.) These bags are sealed in aluminum foil overpouches. The products are then loaded into an autoclaving sterilizer and sterilized at 121° C. for 36 minutes.

The sterilized products are subjected to inspection and release tests. The bag products prepared above are selected and placed on stability test. At each stability time, one bag of each solution is tested for pH, potency, osmolality, physical appearance and particulate matter. The concentration of the drug is determined by a high performance liquid chromatographic (HPLC) method. The results are summarized as follows:

I. Stability of Bags Stored at Various Temperatures and Times

| Test Time | Potency (mg/ml) | pH | Osmolality (mosm/kg) | Visual Inspection | Particulate Matter Particles ≧10 μm | Particles ≧25 m |
|---|---|---|---|---|---|---|
| 25° C./35% RH* | | | | | | |
| Initial | 10.9 | 4.9 | 304 | Pass** | 0 | 0 |
| 3 months | 10.7 | 4.9 | 303 | Pass | 0 | 0 |
| 6 months | 10.6 | 4.9 | 302 | Pass | 0 | 0 |
| 30° C./35% RH* | | | | | | |
| Initial | 10.9 | 4.9 | 304 | Pass | 0 | 0 |
| 3 months | 10.6 | 4.9 | 304 | Pass | 0 | 0 |
| 6 months | 10.4 | 4.8 | 304 | Pass | 0 | 0 |
| 40° C./15% RH* | | | | | | |
| Initial | 10.9 | 4.9 | 304 | Pass | 0 | 0 |
| 1 months | 10.7 | 4.9 | 304 | Pass | 0 | 0 |
| 2 months | 10.5 | 4.9 | 304 | Pass | 0 | 0 |
| 3 months | 10.4 | 4.9 | 306 | Pass | 0 | 0 |
| 6 months | 9.9 | 4.8 | 308 | Pass | 0 | 0 |

*The storage temperature and humidity conditions. RH = Relative Humidity
**Pass: clear colorless solution.

EXAMPLE 2

Example 1 is repeated with the following formulation:

| Ingredient | Amount/ml Solution |
|---|---|
| Esmolol HCl | 11 mg/ml |
| Dextrose | 50 mg/ml |
| Sodium Acetate Trihydrate | 2.8 mg/ml (0.02M) |
| Glacial Acetic Acid | 0.546 mg/ml (0.01M) |
| Sodium Hydroxide/Hydrochloric Acid | pH adjustment to 5.0 |
| Water for Injection, USP | Qs |

EXAMPLE 3

Example 1 is repeated with the following formulation:

| Ingredient | Amount/ml Solution |
|---|---|
| Esmolol HCl | 11 mg/ml |
| Dextrose | 25 mg/ml |
| Sodium Chloride | 2.95 mg/ml |
| Sodium Acetate Trihydrate | 2.8 mg/ml (0.02M) |
| Glacial Acetic Acid | 0.546 mg/ml (0.01M) |
| Sodium Hydroxide/Hydrochloric Acid | pH adjustment to 5.0 |
| Water for Injection, USP | Qs |

All references, including publications, patent applications, and patents, cited herein are hereby incorporated by reference to the same extent as if each reference were individually and specifically indicated to be incorporated by reference and were set forth in its entirety herein.

What is claimed is:

1. An aqueous, sterile pharmaceutical composition suitable for parenteral administration for the treatment of cardiac conditions, having a pH between 3.5 and 6.5 comprising:
    a. 0.1–500 mg/ml methyl-3-[4-(2-hydroxy-3-isopropylamino) propoxy]phenylpropionate hydrochloride (esmolol hydrochloride);
    b. 0.01–2 M buffering agent; and
    c. 1–500 mg/ml osmotic-adjusting agent.
2. The pharmaceutical composition of claim 1, wherein the pH is between 4.5 and 5.5.
3. The pharmaceutical composition of claim 1, wherein the buffering agent comprises at least one of acetate, glutamate, citrate, tartrate, benzoate, lactate, gluconate, phosphate and glycine.
4. The pharmaceutical composition of claim 1, wherein the osmotic-adjusting agent comprises at least one of sodium chloride, dextrose, sodium bicarbonate, calcium chloride, potassium chloride, sodium lactate, Ringer's solution and lactated Ringer's solution.
5. The pharmaceutical composition of claim 3, wherein the osmotic-adjusting agent comprises at least one of sodium chloride, dextrose, sodium bicarbonate, calcium chloride, potassium chloride, sodium lactate, Ringer's solution and lactated Ringer's solution.
6. The pharmaceutical composition of claim 1 comprising:
    a. 0.1–100 mg/ml esmolol hydrochloride;
    b. 0.01–0.5 M buffering agent; and
    c. 1–100 mg/ml osmotic-adjusting agent.
7. The pharmaceutical product of claim 1 comprising:
    a. 100–500 mg/ml esmolol hydrochloride;
    b. 0.5–2 M buffering agent; and
    c. 50–500 mg/ml osmotic-adjusting agent.
8. The pharmaceutical composition of claim 1, wherein the composition is provided in a heat sterilized container.
9. The pharmaceutical composition of claim 8, wherein the container is a vial, ampul, bag, bottle or syringe.
10. The pharmaceutical composition of claim 9, wherein the container is from 1–500 ml in volume.
11. The pharmaceutical composition of claim 4, having a pH of about 5 and comprising about 100–250 mg/ml of esmolol hydrochloride and 0.5–2 M buffering agent and 50–500 mg/ml osmotic-adjusting agent.
12. An aqueous, sterile pharmaceutical composition suitable for parenteral administration for the treatment of cardiac conditions, having a pH of about 5.0 and comprising about 1–20 mg/ml esmolol hydrochloride, 0.02–0.1 M buffering agent and 1–100 mg/ml osmotic-adjusting agent, wherein the osmotic-adjusting agent comprises at least one of sodium chloride, dextrose, sodium bicarbonate, calcium chloride, potassium chloride, sodium lactate, Ringer's solution and lactated Ringer's solution.

13. A method for preparing an aqueous, sterile pharmaceutical composition suitable for parenteral administration for the treatment of cardiac conditions, comprising forming an aqueous composition having a pH between 3.5 and 6.5 comprising 0.1–500 mg/ml methyl-3-[4-(2-hydroxy-3-isopropylamino) propoxy]phenylpropionate hydrochloride (esmolol hydrochloride), 0.01–2 M buffering agent, and 1–500 mg/ml osmotic-adjusting agent in a sealed container and autoclaving for a period of time sufficient to render the composition sterile.

14. The method of claim 13, wherein the composition has a pH between 4.5 and 5.5.

15. The method of claim 13, wherein autoclaving is carried out a temperature ranging from 115° C. to 130° C. for a period of time ranging from 5 to 40 minutes.

16. The method of claim 14, wherein autoclaving is carried out a temperature ranging from 115° C. to 130° C. for a period of time ranging from 5 to 40 minutes.

* * * * *